United States Patent [19]

Schaefer

[11] Patent Number: 4,795,142
[45] Date of Patent: Jan. 3, 1989

[54] PATIENT SUPPORTING TABLE

[75] Inventor: Willi Schaefer, Erlangen, Fed. Rep. of Germany

[73] Assignee: Siemens Aktiengesellschaft, Berlin and Munich, Fed. Rep. of Germany

[21] Appl. No.: 175,586

[22] Filed: Apr. 1, 1988

Related U.S. Application Data

[63] Continuation of Ser. No. 25,656, Mar. 13, 1987, abandoned.

[30] Foreign Application Priority Data

Mar. 20, 1986 [DE] Fed. Rep. of Germany ... 8607769[U]

[51] Int. Cl.[4] ............................................. A61G 13/00
[52] U.S. Cl. .................................................. 269/322
[58] Field of Search .................... 269/322, 328; 5/527

[56] References Cited

U.S. PATENT DOCUMENTS

| | | | |
|---|---|---|---|
| 316,980 | 5/1885 | Knowles | 269/324 |
| 3,615,088 | 10/1971 | Compton | 269/323 |
| 3,631,241 | 12/1971 | Franke | 269/322 |
| 3,813,091 | 5/1974 | Metzger | 269/322 |

FOREIGN PATENT DOCUMENTS

| | | |
|---|---|---|
| 1158663 | 12/1963 | Fed. Rep. of Germany . |
| 1196815 | 7/1965 | Fed. Rep. of Germany . |
| 2204573 | 8/1973 | Fed. Rep. of Germany . |

Primary Examiner—Frederick R. Schmidt
Assistant Examiner—Judy J. Hartman

[57] ABSTRACT

A patient supporting table comprises a table top which is detachably held on a pedestal at one end. The table top is connected to the pedestal by a plug connection so that it can be detached from the pedestal by simply lifting a free end of the table top to detach a first group of plug connectors and then shifting the table top in a direction toward the free end to disconnect a second group of plug-type connections.

2 Claims, 1 Drawing Sheet

PATIENT SUPPORTING TABLE

This is a continuation of application Ser. No. 025,656, filed Mar. 13, 1987, now abandoned.

BACKGROUND OF THE INVENTION

The present invention is directed to a patient supporting table comprising a table top held on one side on a pedestal.

A patient supporting table having a table held by a pedestal is known, and an example is a pedestal which is suspended from the ceiling of the examination room. The table top projects in a cantilever fashion from the pedestal into the room so that good access to the patient is possible.

SUMMARY OF THE INVENTION

The object of the present invention is to provide a patient supporting table having a pedestal supporting a table top in which an easy detachment of the table top from the pedestal is possible without the assistance of tools.

This object is achieved in an improvement in a patient supporting table comprising a table top which is held on a pedestal at one side. The improvement is connecting means on a first end of the table and the pedestal for producing a plug-type connection which requires both lifting and lateral movement for disengaging the table from the pedestal. The connecting means, which is of a plug-type connector, is constructed so that the first end of the table is secured on the pedestal and a free second end is lifted to release a first group of projections from holes and then the table may be shifted to remove a second group from a second group of holes.

In the patient supporting table of the present invention, the table top can be detached from the pedestal by a simple lifting and shifting and be replaced by a different table top. At the same time, the present invention provides protection against damaging the table from lowering the table inadvertently onto an object. When the free second end of the table strikes an impediment on its under surface, it is then lifted without being damaged. When the table top is removed, the table has no cover surfaces and can thus be easily cleaned.

Other objects and advantages of the invention will be readily apparent from the following description, drawings and claims.

DESCRIPTION OF THE PREFERRED EMBODIMENTS

The principals of the present invention are particularly useful in a patient supporting table which has a pedestal 1 that is composed of discrete parts which are extensible in a vertical direction in a telescopic fashion so that the patient supporting table can be adjusted for height. The control of the table and of the allocated X-ray examination apparatus occurs by means of a control box 2 which is attached to the side of the pedestal 1. A table top 3 is held in a cantilevered fashion on an upper surface of the pedestal and, as illustrated, is connected at a first end to the pedestal.

Figure 1:
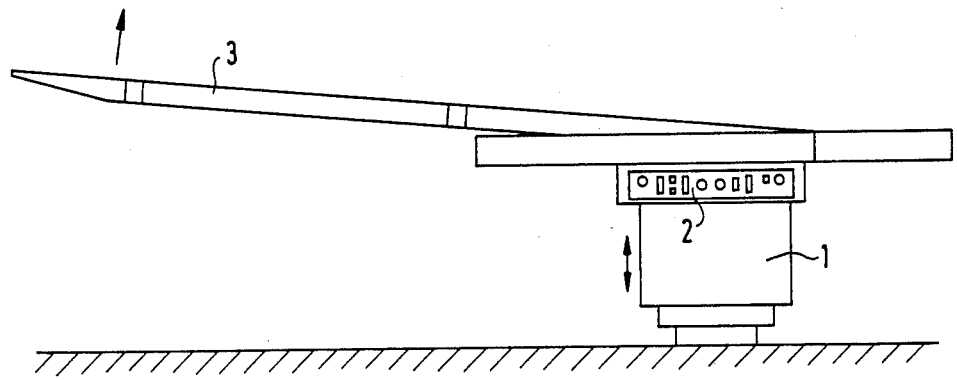
FIG. 1 is a side view of a patient supporting table of the present invention with the table top being partially rotated into an elevated position.

The table top 3 can be easily detached from the pedestal 1 without tools by lifting a free second end, as indicated by the arrow in FIG. 1, and then pulling the table top 3 towards its free second end, or to the left, as illustrated in FIG. 1. The top 3 is connected to the pedestal 1 by a means for connecting which is a plug-type connection.

Figure 2:
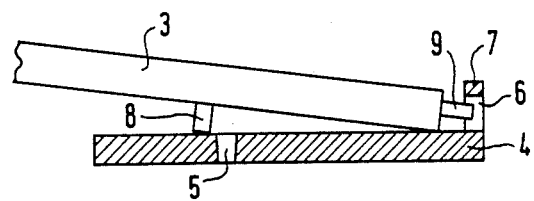
FIG. 2 is a cross sectional view with portions in elevation of the connecting arrangement for the patient supporting table of FIG. 1.

As illustrated in FIG. 2, the plug-type connection is shown in greater detail and includes a plate which is secured on an upper end or surface of the pedestal 1. The plate 4 has a projection 7 at one end. The projection 7 is provided with a plurality of first holes 6, which are preferably two holes, while the plate 4 is provided with a plurality of second holes 5, which are preferably at least two holes. The top 3 has a plurality of pegs with first pegs 9 extended from the first end and being matched in number and position to the first holes 6. Second pegs 8 are matched to the second holes 5, in the position of the table top shown in FIG. 2, and have been lifted at its left second end and, accordingly, can be easily removed from the plate 4. When it is to be connected to the plate, it is shifted to the right with the first pegs 9 entering the first holes 6. When the second pegs 8 overlay the second holes 5, the table can then be lowered so that the pegs engage in the holes.

Given the predetermined pitch angle necessary for disconnecting the table top, the table top 3 is interchangeable. No interlocks of any kind are needed to be actuated for releasing the connection. The actuation of such interlocks is also eliminated when the table top 3 is to be held on the pedestal 1. A table top 3, which has not been properly inserted, can be clearly seen, because the front pegs 8 will not be engaged into the holes 5 so that the free end of the table will be in a visibly higher position than normal.

Although various minor modifications may be suggested by those versed in the art, it should be understood that I wish to employ within the scope of the patent granted hereon, all such modifications as reasonably and properly come within the scope of my contribution to the art.

I claim:

1. A patient supporting table comprising a pedestal, a table top with a first end and a second end, and means for detachably securing the table top at said first end to the pedestal with the second end of the table top being unsupported, said means for detachably securing comprising a plug-type connection being disconnectible by upwardly tilting the unsupported second end of the table top and then shifting the table top in a direction towards the unsupported second end of the table top and away from said pedestal; said plug-type connection including at least two first pegs projecting from the first end of the table top and at least two second pegs projecting at substantially right angles to the first pegs from a bottom surface of the table top at a given distance from the first end of the table top, said pedestal having a plate with a projection extending at substantially a right angle, thereto, surface extending substantially perpendicular to an upper surface of the plate, said shoulder surface having annular edges forming a first hole for each of the first pegs, said upper surface of said plate having annular edges forming a second group of second holes for receiving each of the second pegs; said first holes having a width greater than the width of the first pegs and said second holes having a width greater than the width of the second pegs; said annular edges of the shoulder surface having upper portions remote from said upper surface and said annular edges in said upper surface of the plate having neighboring portions proximate said shoulder surface; and the first pegs engaging said upper portions of said first holes and the second pegs engaging said neighboring portions of said second holes, when the table top is secured to said pedestal.

2. A patient support table comprising a pedestal, a table top with a bottom surface, a first end and a second end, and means for detachably securing the table top at said first end to the pedestal with the second end of the table top being unsupported, said means for detachably securing comprising a plate being secured on the pedestal, said plate having an upper surface with a projection extending from one end at substantially a right angle to said upper surface extending substantially perpendicular to said upper surface, at least one first peg, extending from the end of the table top and being received in at least one respective aperture in said shoulder surface and at least one second peg extending from the bottom surface of the table top at substantially a right angle thereto at a fixed distance from the first peg and being received in at least one respective aperture in the plate upper surface of the to form a plug connection means between the table top and plate whereby the table is disconnected from the plate by upwardly tilting the unsupported second end of the table top to disconnect each second peg from its aperture in the plate, and then shifting the table top in a direction towards the unsupported second end of the table top and away from said pedestal to disconnect each first peg from its aperture in the shoulder surface.

* * * * *